(12) United States Patent
Liu (10) Patent No.: US 9,937,193 B2
(45) Date of Patent: Apr. 10, 2018

(54) METHOD FOR TREATING A CANCER

(71) Applicant: National Yang-Ming University, Taipei (TW)

(72) Inventor: Jin-Hwang Liu, Tapei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 15/095,508

(22) Filed: Apr. 11, 2016

(65) Prior Publication Data

US 2016/0296545 A1 Oct. 13, 2016

Related U.S. Application Data

(60) Provisional application No. 62/145,305, filed on Apr. 9, 2015.

(51) Int. Cl.

| | | |
|---|---|---|
| *G01N 33/574* | (2006.01) | |
| *A61K 31/19* | (2006.01) | |
| *A61K 31/704* | (2006.01) | |
| *A61K 31/167* | (2006.01) | |
| *A61K 31/502* | (2006.01) | |
| *A61K 45/06* | (2006.01) | |
| *A61K 31/20* | (2006.01) | |

(52) U.S. Cl.
CPC .......... *A61K 31/704* (2013.01); *A61K 31/167* (2013.01); *A61K 31/20* (2013.01); *A61K 31/502* (2013.01); *A61K 45/06* (2013.01)

(58) Field of Classification Search
CPC .... A61K 31/19; A61K 31/704; A61K 31/167; A61K 31/502; G01N 33/574
USPC ......................................................... 435/7.23
See application file for complete search history.

(56) References Cited

FOREIGN PATENT DOCUMENTS

WO    WO 2003070234    *   8/2003    ............. A61K 31/13

OTHER PUBLICATIONS

Berenbaum (Clin. Exp Immunol. 28:1-18, 1977).*
Wiesenthal (http://weisenthal.org/feedback.html, Feb. 4, 2002).*
Wang et al. (PLoS ONE, Published Sep. 30, 2013, 8(9): e76662, pp. 1-12).*
Catalano et al. (Journal of Endocrinology, 2006, 191: 465-472).*

* cited by examiner

*Primary Examiner* — Yan Xiao
(74) *Attorney, Agent, or Firm* — Juan Carlos A. Marquez; Marquez IP Law Office, PLLC (57) ABSTRACT

The present invention relates to a method for treating a cancer with the combination of a topoisomerase II inhibitor (TOP2 inhibitor) and a histone deacetylation inhibitor (HDACi), provides synergistic cancer cell-killing effects, and prolonged overall survival, especially when the expression of checkpoint kinase 1 (CHK-1) is low.

3 Claims, 7 Drawing Sheets

METHOD FOR TREATING A CANCER

RELATED APPLICATION

The present application claims priority under 35 U.S.C. § 119(e) to U.S. Provisional Patent Application No. 62/145,305 filed Apr. 9, 2015, the content of which is herein incorporated by reference in its entirety.

FIELD OF THE INVENTION

The present invention generally relates to a method for treating a cancer; particularly, the present invention relates to a method for treating a cancer with a combination of an anti-cancer drug and a histone deacetylation inhibitor (HDACi) after checking the expression of checkpoint kinase 1 (CHK-1).

BACKGROUND OF THE INVENTION

Hepatocelluar carcinoma (HCC), of which the prevalence in Asia Pacific area including Taiwan is high and is an important cause of death (El-Serag H B, Rudolph K L. Hepatocellular carcinoma: epidemiology and molecular carcinogenesis. *Gastroenterology* 2007; 132: 2557-2576). Surgical resection remains the way most promisingly leading to long-term survival; however, only 20% or less of the patients with HCC could undertake surgical resection (Hung H. Treatment modalities for hepatocellular carcinoma. *Curr Cancer Drug Targets* 2005; 5: 131-138.). There is still an unmet need for systemic therapies for advanced HCC (Lopez P M, Villanueva A, Llovet J M. Systematic review: evidence based management of hepatocellular carcinoma—an updated analysis of randomized controlled trials. *Aliment Pharmacol Ther* 2006; 23: 1535-1547) even after sorafenib was proven to improve overall survival (OS) in patients with advanced HCC (Llovet J M, Ricci S, Mazzaferro V, et al. Sorafenib in advanced hepatocellular carcinoma. *N Engl J Med* 2008; 359: 378-390). Sorafenib significantly prolonged OS of patients with advanced HCC; however, the increment was small especially for patients in Asia Pacific area where around 70% of HCC are HBV associated, with median OS of 6.5 months in the sorafenib arm compared with 4.2 months in the placebo arm (Cheng A L, Kang Y K, Chen Z, Tsao C J, Qin S, Kim J S, Luo R, Feng J, Ye S, Yang TS, Xu J, Sun Y, Liang H, Liu J, Wang J, Tak W Y, Pan H, Burock K, Zou J, Voliotis D, Guan Z. Efficacy and safety of sorafenib in patients in the Asia-Pacific region with advanced hepatocellular carcinoma: a phase III randomised, double-blind, placebo-controlled trial. Lancet Oncol. 2009 January; 10(1):25-34).

There is still a need for new systemic therapies for a cancer with synergistic efficacies.

SUMMARY OF THE INVENTION

This invention is based on the unexpected finding that the combination of a topoisomerase II inhibitor (TOP2 inhibitor), such as doxorubicin or hydrazaline, and a histone deacetylation inhibitor (HDACi), such as suberoylanilide hydroxamic acid (SAHA) or valproic acid, provides synergistic cancer cell-killing effects, and prolonged overall survival.

Furthermore, it is also found in the invention that checkpoint kinase 1 (CHK-1) is potentially a biomarker of synergistic cytotoxicity of HDACi in combination with DSB-inducing chemotherapeutics, such as a topoisomerase II inhibitor (TOP2 inhibitor), when the expression of CHK-1 is low in the subject.

Accordingly, in one aspect, the present invention provides method for treating a cancer and prolonging the overall survival of a subject suffering a cancer comprising: providing a cancer cell sample of the subject, and determining the expression of CHK-1 of the sample, wherein the attenuation of activated CHK-1 used as a biomarker; administering the subject, if the attenuation of activated CHK-1 is found in the sample, with a combination of a topoisomerase II inhibitor (TOP2 inhibitor) and a Histone deacetylation inhibitor (HDACi) at the ratio to provide synergistic cancer cell-killing effects and prolonged overall survival.

In one example of the invention, the HDACi is suberoylanilide hydroxamic acid (SAHA) or valproic acid (VA).

In one example of the invention, the TOP2 inhibitor is doxorubicin (Doxo) or hydrazaline (HZ).

In another aspect, the invention provides a pharmaceutical composition comprising a combination of valproic acid (VA) and hydrazaline (HZ) at the ratio to provide synergistic cancer cell-killing effects and prolonged overall survival.

In one example of the invention, the cancer is hepatocellular carcinoma (HCC).

BRIEF DESCRIPTION OF THE DRAWINGS

The foregoing summary, as well as the following detailed description of the invention, will be better understood when read in conjunction with the appended drawing. In the drawings:

The foregoing summary, as well as the following detailed description of the invention, will be better understood when read in conjunction with the appended drawing. In the drawings:

FIG. 5 (C) shows another independent test for CHK-1 expression, indicating the similar results.

DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The drugs targeting topoisomerase II (TOP2) have been in clinical use for many years, such as etoposide, doxorubicin and mitoxantrone and are found to reduce the toxicity when used in combination of other anticancer agents, including chemotherapeutic agents.

Histone deacetylation inhibitors (HDACi) are involved in acetylation and degradation of Sae2 (orthologue of human CtIP) required for DNA double strand break repair (Robert T, Vanoli F, Chiolo I, Shubassi G, Bernstein K A, Rothstein R, Botrugno O A, Parazzoli D, Oldani A, Minucci S, Foiani M. HDACs link the DNA damage response, processing of double-strand breaks and autophagy. Nature. 2011; 471 (7336):74-9). HDACis may thus abort DNA repair in tumor cells after chemotherapy and promote efficacy of chemotherapy which may lead to double strand DNA break. Examples of HDACis include but are not limited to suberoylanilide hydroxamic acid (SAHA), Valproic acid (VA) and hydrazaline (HZ). Valproic acid (VA) and hydrazaline (HZ) can function as HDACis and may after chemotherapy abort DNA repair in tumor cells and thus promote efficacy of chemotherapy.

It is unexpectedly found in the invention that attenuation of CHK-1 expression in T-ALL cells and hepatocellular cells was associated with proapoptosis and hampering of DNA repair when double strand DNA breaks were chemotherapy-induced. It was evidenced in the invention that the synergistic cell-killing effects of the combination of doxorubicin (a TOP2 inhibitor) and suberoylanilide hydroxamic acid (SAHA) (an HDACi) on a CTV-1lymphoblastic cell line of which phosphorylation of CHK-1 were negatively affected by SAHA. However, in the SAHA-treated T ALL cells, the repair of doxorubicin-induced double strand DNA break (DSB) was initiated with increased H2AX. However, although SAHA increased H2AX and acetyl H2AX, DSB repair was aborted by decreasing G2/M arrest of cells and hampering the nuclear entry of CtIP, a DNA repair protein. SAHA eventually synergistically increased doxorubicin-induced apoptosis with the induction of cleaved caspases 8 and 9. In addition, valproic acid showed synergistic effects with doxorubicin in inducing cell death of Hep3 and PLC hepatocellular carcinoma (HCC) cells, HDACi thus synergistically impaired the topoisomerase II-induced DSB repair and induced apoptosis by eliciting DNA repair with H2AX; however, aborted the DNA repair and induced apoptosis by hampering the nuclear entry of CtIP. Attenuation of activated CHK-1 may be potentially a biomarkers of synergistic cytotoxicities of HDACi and DSB-inducing chemotherapeutics.

Accordingly, the invention provides A method for treating a cancer and prolonging the overall survival of a subject suffering a cancer comprising:
providing a cancer cell sample of the subject, and determining the expression of (CHK-1) of the sample, wherein the attenuation of activated CHK-1 used as a biomarker;
providing a cancer cell sample of the subject, and determining the expression of checkpoint kinase 1 (CHK-1) of the sample, wherein the attenuation of activated CHK-1 is used as a biomarker; and
administering the subject, if the attenuation of activated CHK-1 is found in the sample, with a combination of a topoisomerase H inhibitor (TOP2 inhibitor) and a Histone deacetylation inhibitor (HDACi) at the ratio to provide synergistic cancer cell-killing effects and prolonged overall survival.

It is also unexpectedly found in the invention that a pharmaceutical composition comprising a combination of Valproic Acid (VA) and Hydralazine (HZ) providing synergistic cancer cell-killing effects and prolonged overall survival. It was evidenced in the example that the combination of VA and HZ-modulated chemotherapy with less than the usual chemotherapy shows an encouraging effective survival benefit in advanced HCC with manageable toxicities.

Accordingly, the present invention also provides a method for treating a subject suffering a cancer, optionally treated with a chemotherapy, comprising administering a subject in need thereof with a combination of Valproic Acid (VA) and Hydralazine (HZ) at the ratio to provide synergistic cancer cell-killing effects and prolonged overall survival.

The present invention provides a method for treating a cancer and prolonging the survival of a subject suffering a cancer treated with a chemotherapy, comprising administering a subject in need thereof with a combination of valproic acid (VA) and hydrazaline (HZ) at the ratio to provide synergistic cancer cell-killing effects and prolonged overall survival.

In one example of the invention, the cancer is hepatocellular carcinoma (HCC).

The pharmaceutical composition of the invention may be administered in any route that is appropriate, including but not limited to parenteral or oral administration. The pharmaceutical compositions for parenteral administration include solutions, suspensions, emulsions, and solid injectable compositions that are dissolved or suspended in a solvent immediately before use. The injections may be prepared by dissolving, suspending or emulsifying one or more of the active ingredients in a diluent. Examples of said diluents are distilled water for injection, physiological saline, vegetable oil, alcohol, and a combination thereof. Further, the injections may contain stabilizers, solubilizers, suspending agents, emulsifiers, soothing agents, buffers, preservatives, etc. The injections are sterilized in the final formulation step or prepared by sterile procedure.

According to the invention, the composition may be administered through oral route, wherein the composition may be in a solid or liquid form. The solid compositions include tablets, pills, capsules, dispersible powders, granules, and the like. The oral compositions also include gargles which are to be stuck to oral cavity and sublingual tablets. The capsules include hard capsules and soft capsules. In such solid compositions for oral use, one or more of the active compound(s) may be admixed solely or with diluents, binders, disintegrators, lubricants, stabilizers, solubilizers, and then formulated into a preparation in a conventional manner. When necessary, such preparations may be coated with a coating agent, or they may be coated with two or more coating layers. On the other hand, the liquid compositions for oral administration include pharmaceutically acceptable aqueous solutions, suspensions, emulsions, syrups, elixirs, and the like. In such compositions, one or more of the active compound(s) may be dissolved, suspended or emulsified in a commonly used diluent (such as purified water, ethanol or a mixture thereof, etc.). Besides such diluents, said compositions may also contain wetting agents, suspending agents, emulsifiers, sweetening agents, flavoring agents, perfumes, preservatives and buffers and the like.

The present invention is further illustrated by the following examples, which are provided for the purpose of demonstration rather than limitation.

Example 1

Patients

The protocol of the clinical study was reviewed and approved by the institute research board of Taipei Veterans General Hospital, Taipei, Taiwan. Patients aged more than 20 years with unresectable or metastatic HCC proven by pathology were recruited with an informed consent.

A Simon 2-stage phase II trial was designed with Type I error rate of 0.05 and 80% power. The primary end was overall survival (OS) of patients with advanced hepatocellular carcinoma (HCC). The treatment protocol was valproic acid (VA) and hydrazaline (HZ)-modulated gemcitabine and cisplatin as the $1^{st}$-step chemotherapy, followed by VA and HZ-modulated doxorubicin and dacarbazine as the $2^{nd}$-step chemotherapy. The second ends of this trial were response rates, progression-free survivals (PFSs), and toxicities. In thirty-one patients, eleven patients failed or were intolerant to previous sorafenib. All patients received GCGG but only 26 could receive DoxDTIC treatment. Eligibility also included Child Pugh A/B, performance status≤2; being chemonaive but regardless of previous sorafenib; having failed or being not suitable for local therapies; ECOG performance status≤2; having adequate renal, hematological function, as indicated by a platelet count of >75×10$^9$/L, hemoglobulin>85 g/L.

Patients were treated with oral VA 200 mg thrice per day (twice for body weight less than 50 kg) and HZ 12.5 mg twice per day, during all the trial days. For the $1^{st}$-step chemotherapy (GCGG), patients were treated with gemcitabine 800 mg/m$^2$ on D 1, 8, and 15; cisplatin 70 mg/m$^2$, adjusted with renal function on D 1. After disease progression, if patients were still met the initial eligibility, they entered the $2^{nd}$-step chemotherapy (DoxDTIC) with intravenous doxorubicin 45 mg/m$^2$ with dacarbazine 450 mg/m$^2$ on D1 in a 21-day cycle.

Statistical Evaluations

Based on a phase III randomised trial on sorafenib in patients in the Asia-Pacific region with advanced HCC, the median overall survival was 6.5 months in patient treated with sorafenib (Cheng A L, Kang Y K, Chen Z, Tsao C J, Qin S, Kim J S, Luo R, Feng J, Ye S, Yang T S, Xu J, Sun Y, Liang H, Liu J, Wang J, Tak W Y, Pan H, Burock K, Zou J, Voliotis D, Guan Z. Efficacy and safety of sorafenib in patients in the Asia-Pacific region with advanced hepatocellular carcinoma: a phase III randomised, double-blind, placebo-controlled trial. Lancet Oncol. 2009 January; 10(1): 25-34). In this study, Simon's minimax two-stage design (Simon R. Optimal two-stage designs for phase II clinical trials. 1989 Controlled Clinical Trials 10:1-10) was used to evaluate the effectiveness of the protocol. Software by Dr. Ivanova from University of North Carolina at Capel Hill was used in the design. The null hypothesis that the 50% of patients survived longer than 6.5 months would be tested against a one-sided type I error of 0.05 and power of 0.8 when actually 70% patients survived longer than 6.5 months. In the first stage, if it is fewer than 13 out of 23 patients survived over 6.5 months, the study would be stopped. Otherwise, 14 additional patients will be accrued for a total of 37. If more than 23 out of 37 patients survived longer than 6.5 months, this protocol is assumed to be effective.

Results

Thirty-one patients were enrolled. The patients' characteristics were given in Table 1. All patients received GCGG but only 26 could receive DoxDTIC treatment.

Figure 1:
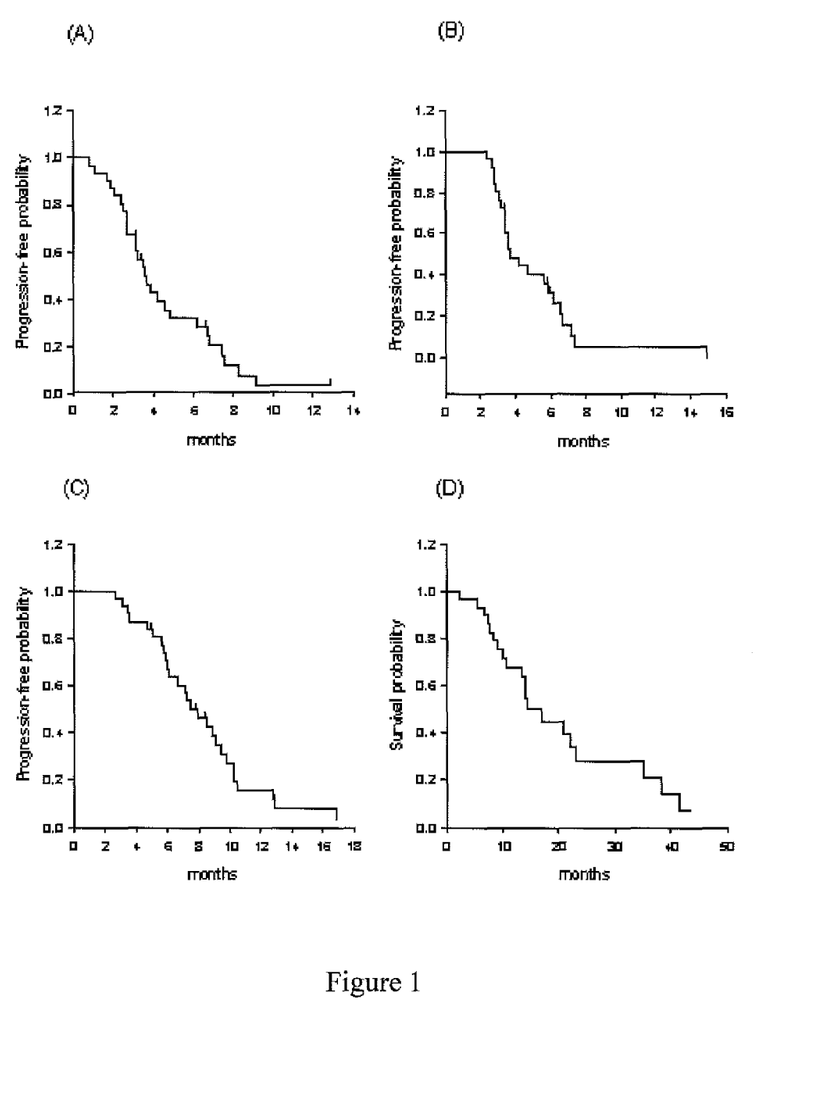
FIG. 1 shows that progression free survivals of patients treated with VA and HZ modulated GCGG (A), DoxDTIC (B), and the 2-step treatments (C), and overall survival of the patients with advanced HCC following the VA and HZ modulated 2-step chemotherapy (D).

After treatment, the response rates of the patients by the Response Evaluation Criteria in solid tumors were given in Table 2, and the related adverse effects caused by chemotherapy in the patients were given in Table 3. The progression free survivals (PFSs) of the patients treated with VA and HZ modulated GCGG (A), DoxDTIC (B), and the 2-step treatments (C), and overall survival of the patients with advanced HCC following the VA and HZ modulated 2-step chemotherapy (D) are shown in FIG. 1.

TABLE 1

Patients' Characteristics

| | |
|---|---|
| Median age, years (range) | 57 (38-77) |
| Male, n (%) | 23 (74.1) |
| ECOG PS, n (%) | |
| 0 | 9 (29.0) |
| 1 | 17 (54.8) |
| 2 | 5 (16.1) |
| Macroscopic vascular invasion, n (%) | |
| yes | 12 (38.7) |
| no | 19 (61.3) |
| Extrahepatic spread, n (%) | 29 (93.5) |
| Sites, n (%) | |
| lung | 17 (54.8) |
| lymph node | 9 (29.0) |
| brain | 2 (6.4) |
| Bone and/or spine | 4 (12.8) |
| Stomach and/or intestine | 3 (9.6) |
| diaphragm | 3 (9.6) |
| Hepatic vein and/or IVC | 2 (6.4) |
| Peritoneal carcinomatosis | 3 (9.6) |
| Right ventricle | 1 (3.2) |
| Hepatitis virus infection | |
| HBV | 22 (70) |
| HCV | 2 (6.4) |
| HBV + HCV | 1 (3.2) |
| None | 6 (19.3) |
| BCLC stage C, n (%) | |
| C | 29 (93.5) |
| B | 2 (6.4) |
| Child-Pugh score | |
| 5 | 13 (41.9) |
| 6 | 11 (35.4) |
| 7 | 6 (19.3) |
| 8 | 1 (3.2) |
| Max diameter of intrahepatic HCCs (cm) | |
| 1.5-3 | 4 (12.9) |
| 3.1-5- | 9 (29.0) |
| 5.1-7.5 | 8 (25.8) |
| 7.6-10 | 7 (22.5) |
| >10 | 3 (9.6) |

TABLE 1-continued

Patients' Characteristics

Previous treatment

| | | |
|---|---|---|
| Liver resection | 12 | (38.7) |
| Liver transplantation | 3 | (9.6) |
| TACE | 23 | (74.2) |
| Sorafenib | 11 | (35.4) |

TABLE 2

Response rates by Response Evaluation Criteria in Solid Tumors

| | VA + HZ/GCGG (n = 31) | VA + HZ/DoxDTIC (n = 26) |
|---|---|---|
| Complete response | 0 (0) | 0 (0) |
| Partial response | 8 (25.8) | 6 (23.0) |
| Stable response | 17 (54.8) | 13 (50.0) |
| Progression disease | 6 (19.3) | 7 (26.9) |
| DCR | 25 (80.6) | 20 (76.9) |
| 50% AFP reductioin | 10 (32.2) | 11 (42.3) |

TABLE 3

Chemotherapy-related adverse effects

| | VA + HZ/GCGG (n = 31) | | VA + HZ/DoxDTIC (n = 26) | |
|---|---|---|---|---|
| | All, n(%) | Grade 3/4, n(%) | All, n(%) | Grade 3/4, n(%) |
| Hemorrage, UGI | 1 (3.2) | 1 (3.2) | 1 (3.8) | 1 (3.8) |
| Neutropenic fever | 2 (6.4) | 2 (6.4) | 5 (19.2) | 2 (7.6) |
| Liver dysfunction | 3 (9.6) | 3 (9.6) | 16 (61.5) | 0 (0) |
| Neutropenia | 25 (80) | 17 (54.8) | 24 (92) | 15 (57.6) |
| Thrombocytopenia | 25 (80) | 8 (25.8) | 15 (57.6) | 7 (26.9) |
| Anemia | 30 (96.7) | 50.6 (25.8) | 24 (92) | 3 (11.5) |

Survival

The median follow up time is 14.0 months (3.2 to 45 months). The median PFSs were 3.54 months (95% CI, 2.7 to 4.3) for the 31 patients treated with VA/HZ-modulated GCGG treatment and 3.74 months (95% CI, 2.67-4.81) for the 26 patients treated with VA/HZ-modulated DoxDTIC. The 2-step PFS of the 31 patients was 7.98 months (95% CI, 6.20-9.77) from the start of VA/HZ-modulated GCGG (31 patients) to disease progression either just failing GCGG and being unable to undertake further DoxDTIC (5 patients), or failing both GCGG and the following DoxDTIC (26 patients).

In the first stage of the Simon two stage design, we recruited 23 patients, 20 patients had survivals longer than 6.5 months; therefore, additional 8 patients were recruited and 27 out of the total 31 (87%) patients had survivals longer than 6.5 months. The study was then early terminated for the goal of 70% had been achieved. The median OS was 17.5 months (95% CI, 10.0 to 25.0). Drug related toxicities included cytopenias, neutropenic fever and liver dysfunction with neutropenia and thrombocytopenia were the dose-limiting toxicities. The response rate (RR) of VA and HZ-modulated GCGG was 8/31 (25.8%) and disease control rate (DRR), 25/31 (80.6%), while VA and HZ-modulated DoxDTIC had RR of 5/26 (23%) and disease control rate of 20/26 (76.9%). Response rate of VA and HZ-modulated of either GCGG or DoxDTIC is 13/31 (42%).

The progression free survivals (PFSs) of the patients treated with VA and HZ are shown in FIG. 1. It was concluded that the VA and HZ-modulated chemotherapy with less than the usual chemotherapy show an encouraging effective survival benefit in advanced HCC with manageable toxicities. It is concluded that the PFS and OS by oxaliplatin or irinotecan-containing adjuvant chemotherapy following resection or ablation of metachronous CLMs were improved.

Example 2

Materials and Methods

Drug Treatments and Antibodies

Suberoylanilide hydroxamic acid (SAHA) (Sigma-Aldrich, MO) stored at −20° C. at 10 mM in dimethyl sulfoxide (DMSO) and Doxorubicin (Doxo) (Sigma-Aldrich, MO) at 3.6 mM solution were used as stock solutions. SAHA at the final concentrations of 1 µM led to 50% cell death in the three-day growth of CTV-1. Doxo at the final concentrations of 0.09 µM, 1.79 µM, 1.58 µM, and 1.03 µM respectively led to 50% cell death in the three-day growth of CTV-1, J5, PLC and Hep3B cells. Valproic acid (VPA) (Sigma-Aldrich, MO) at $10^{-2}$ M in dimethyl sulfoxide (DMSO), was stocked at −20° C. Fresh dilution of chemicals were prepared before the experiments. VPA at the final concentrations of 28.67, 26.67 and 38.87 µM, respectively led to 50% cell death in the three-day growth of J5, PLC and Hep3B respectively.

Cell Lines

CTV-1, Molt-3, THP-1, MCR-5, J5, LPC and Hep3B cell lines were obtained from the American Type Culture Collection (Rockville, Md.). CTV-1 and Molt-3 and were grown in RPMI 1640 medium supplemented with 10% fetal bovine serum (FBS); THP-1, MCR5, J5, LPC and Hep3B were grown in Dulbecco's modified Eagle's medium (DMEM, Gibco, Grand Island, N.Y.) supplemented with 10% FBS. All were grown at 37° C. in a humidified atmosphere containing 5% $CO_2$.

CTV-1 was segregated with T acute lymphoblastic leukemia and THP-1, with acute myeloid leukemia, according to their expression profiles (Andersson, 2005); Molt-3 is a T acute lymphoblastic leukemia and MRC-5, normal fetal lung fibroblasts cell line (ATCC CCL 171), J5, LPC and Hep3B are HCC cell lines.

Isobologram

Dose-response interactions between SAHA and Doxo, or VPA and Doxo were evaluated using the isobologram method of Steel and Peckham (Steel, 1979). The theoretical basis of the isobologram and the procedure for making the isobologram were described elsewhere (Akutsu, 2002; Kano, 1988).

According to the dose-response curves of SAHA or VPA, and Doxo, 'an additive envelope' was constructed. The location of the iso-effect dose points related to additive envelope were used to determine the interactive effects of in vitro drug combinations. When the data points of drug combination fall within the area surrounded by lines of the additive envelope, the combination was regarded as additive. When the data points fall to the left of the envelope, the combination was regarded as having a synergistic effect. When the points fall to the right of the envelope, but within the square or on the line of the square, the combination was regarded as having a sub-additive effect, i.e. the combination was superior or equal to a single agent, but was less than additive. When the points fell outside the square, the combination was regarded as having a protective effect, i.e. the combination was inferior to a single agent in cytotoxicity. Both sub-additive and protective effects were regarded as being antagonistic.

Apoptosis Assays

Terminal deoxynucleotidyl transferase dUTP nick end labeling (TUNEL) to detect DNA fragments and was used to apoptosis assay. We used the TACS® TdT kit (R&D, MN) according to the manufacturer's protocol.

Western Blot Analyses

After treatment for the indicated time with SAHA, Dox, or both at the concentration of IC50, cells were lysed with 2× sodium dodecyl sulfate (SDS) buffer supplemented with protease inhibitors and subjected to a SDS-polyacrylamide gel electrophoresis (PAGE).

Subcellular Localization of γH2X and CtIP Visualized by Laser Scanning Confocal Microscopy Cells treated for the indicated time were fixed and doubly immunofluorescence-stained for γH2X and CtIP with mouse anti-γH2A.X (1:500) (Ser139)(05-636, Merk Millipore) and rabbit anti-CtIP (1:500) (Sc-22838, Santa Cruz) antibodies, coupled with donkey fluorescein-conjugated anti-mouse and TRITC-conjugated anti-rabbit antibodies (Jackson ImmunoResearch, West Grove, Pa.), respectively. The cells doubly labeled were then visualized using a Leica TCS-SP2 confocal scanning microscope equipped with an acousto-optical tunable filter and a Plan-Apochromat oil-immersion objective with a 63×/1.32 numeric aperture (Leica Microsystems, Bensheim, Germany). Images were acquired with Leica TCSNT software.

Results

1. Synergistic Cytotoxicities of Combinations of SAHA and Doxo in CTV-1 and Molt-3 T-ALL Cells and in Hep3B HCC Cells.

By isobologram analysis, all data points of iso-effect dose with SAHA and Doxo combinations administered in CTV-1 and Molt-3 T-ALL cells fell in the area of supra-additivity and implied an effect of synergistic toxicities.

In HCC cells, synergistic effects of VPA in combination with Doxo was found in Hep3B cells, while additive effects in J5 and antagonistic effects in PLC cells.

Figure 2A:
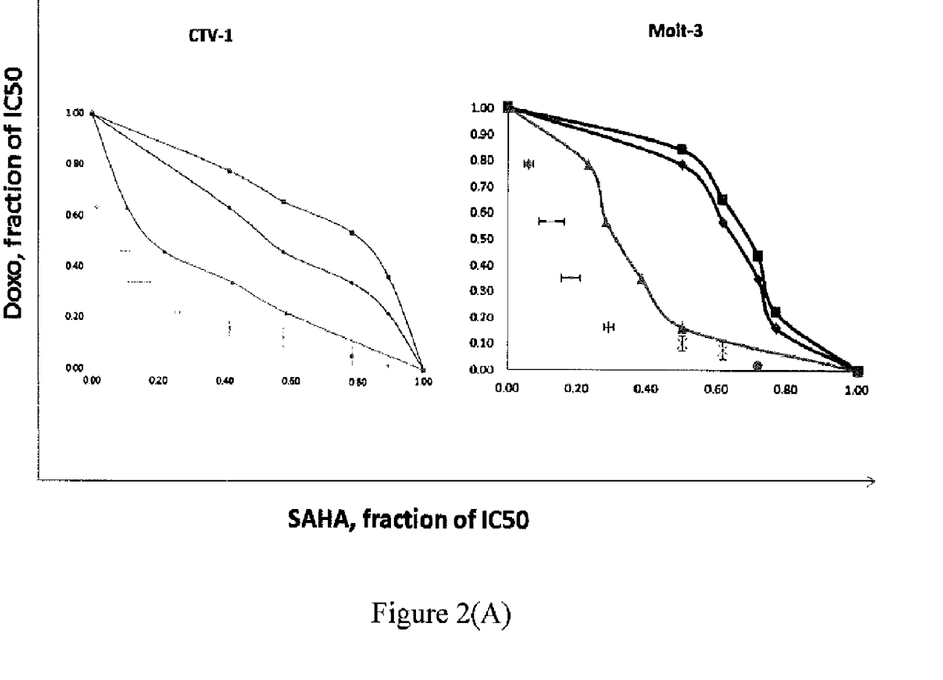
FIG. 2(A) provides the results of the isobolograms analysis for SAHA in combination with Doxo in CTV-1 and Molt-3 T-ALL cells (wherein the data are presented as means±SE for at least three independent experiments).
Figure 2B:
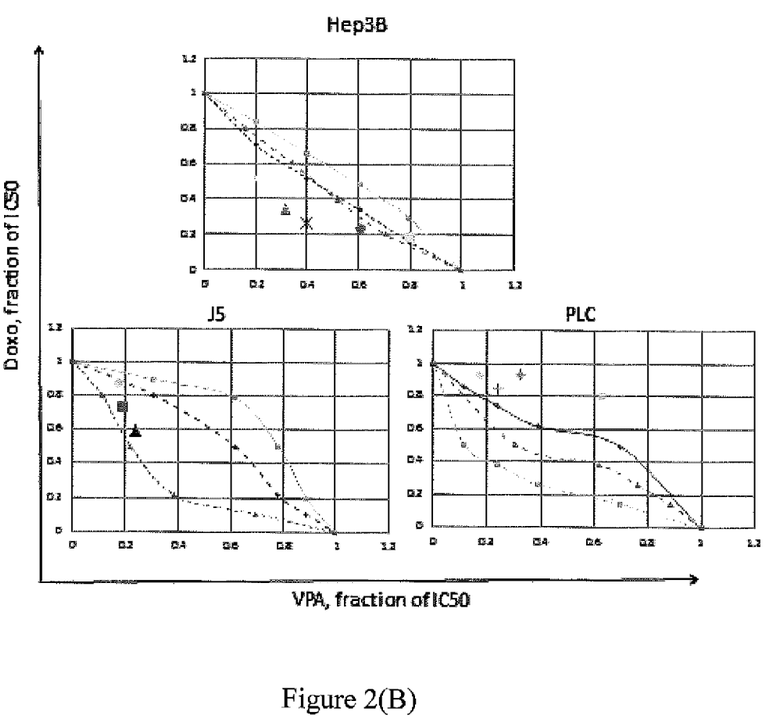
FIG. 2(B) provides the results of the isobolograms analysis for VPA in combination with Doxo in J5, PLC and Hep3B HCC cells (wherein the data are presented as means±SE for at least three independent experiments).

As shown in FIG. 2, the survival of cells was evaluated with 2-day culture by MTT tests. For both CTV-1 and Molt-3 cells, all the iso-effect data points of combinations of Doxo and SAHA at indicated IC50 fractions fell in the area of synergism as shown in FIG. 2(A). For J5 cells, the iso-effect data showed that the combination of Doxo and VPA at indicated 1050 fractions fell in the area of additivity; for PLC cells, in the area of antagonism; while for Hep3B cells, fell in the area of synergism, see FIG. 2(B). The additive envelopes were constructed according to isobologram method of Steel and Peckham (Steel & Peckham. Exploitable mechanisms in combined radiotherapy-chemotherapy: the concept of additivity. Int J Radiat Oncol Biol Phys 1979; 5:85-91).

2. SAHA Sensitized CTV-1 Cells to Doxo-Induced Apoptosis.

Figure 3:
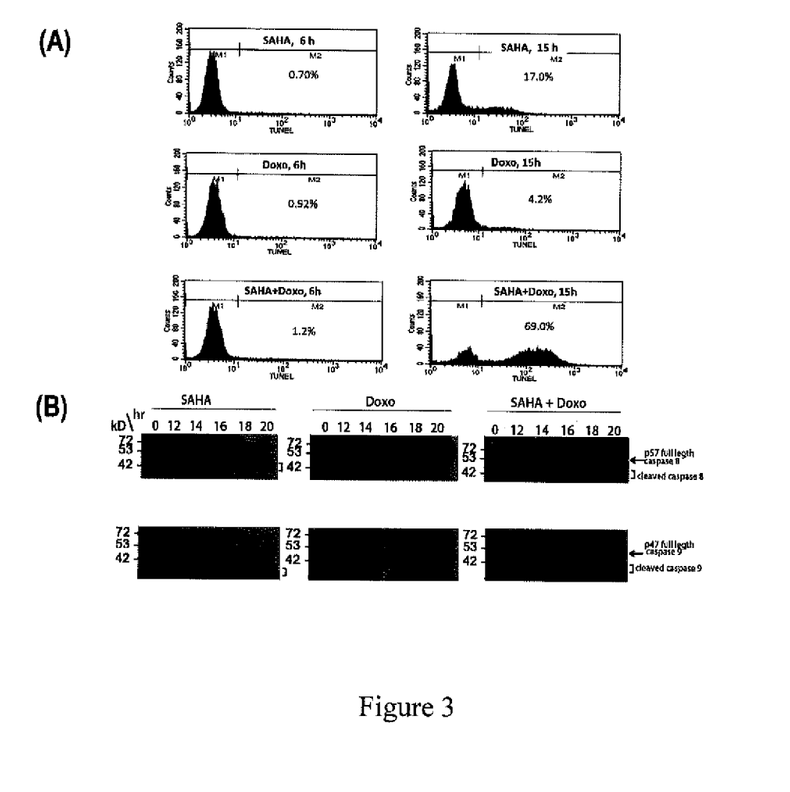
FIG. 3 shows that SAHA sensitized CTV-1 cells to doxo-induced apoptosis, wherein the apoptosis was found with the increased M2 fractions by TUNEL assay (A), and the increased cleavage of caspase 8 and/or 9 by western blot (B).

With 15-h cultures, the apoptosis fraction was significantly increased with combination of SAHA and Doxo. The increased cleaved fractions of caspase 8 and caspase 9 became obvious 16 hrs after treatment with either SAHA or combination of SAHA and Doxo at IC50s. As shown in FIG. 3, SAHA sensitized CTV-1 cells to doxo-induced apoptosis. The apoptosis was evidenced with the increased M2 fractions by TUNEL assay (A), and the increased cleavage of caspase 8 and/or 9 by western blot (B).

3. SAHA Restrained CtIP from Entering Nuclei in Sensitive CTV-1 Cells but not in Normal Fibroblasts.

After a 12-hour treatment with SAHA, it was found that green fluorescence (FITC)-labeled CtIP, red fluorescence (TRITC)-labeled γH2X, and the DAPI-stained nuclei were visualized under co-focal microscopy (no figure shown), indicating. DNA break in terms of revealed by γH2X stain occurred.

4. SAHA Increased the Cell Populations in S Phase.

Figure 4:
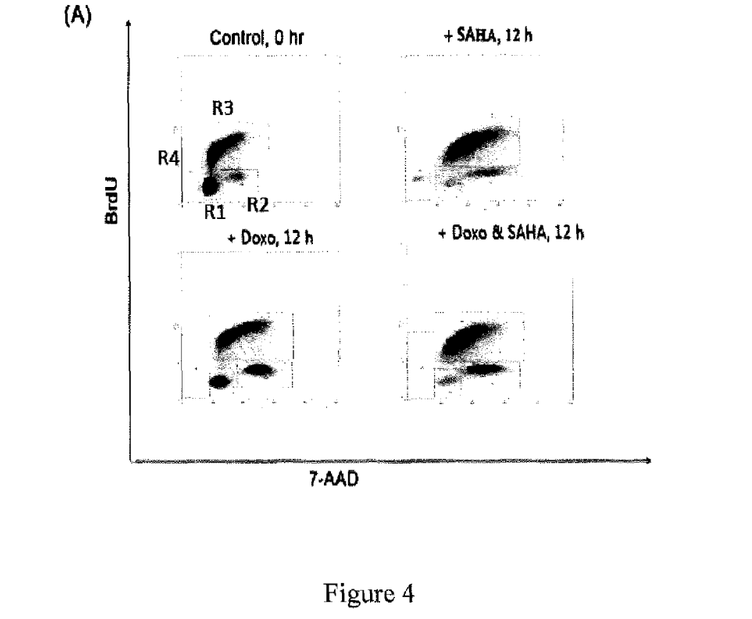
FIG. 4 A provides the cell cycle distributions of CTV-1 after 12-hour treatment with doxorubicin (Doxo), suberoylanilide hydroxamic acid (SAHA) at IC50 or combinations, analyzed with BrdU assay (* denotes p<0.05, comparing cell percentages between after Doxo and Doxo plus SAHA treatment).

The cell populations of CTV-1 were analyzed with BrdU assay after 12-hour treatment with doxorubicin (Doxo), suberoylanilide hydroxamic acid (SAHA), and Doxo & SAHA. As shown in FIG. 4, the cell population in G0G1, G2M, S and subG0 phases in n each plot, R1, R2, R3 and R4 respectively. It was also found that SAHA decreased CTV-1 cells in G0G1 cycle arrest with increase in S phase.

The cell cycle distributions of CTV-1 after 12-hour treatment with doxorubicin (Doxo), suberoylanilide hydroxamic acid (SAHA) at IC50 or combinations are given in Table 4.

TABLE 4

| Treatment | G0G1 | S | G2M | SubG0 |
|---|---|---|---|---|
| Control (vehicles) | 47.4 ± 4.1 | 43.1 ± 4.0 | 6.3 ± 2.1 | 0.13 ± 0.03 |
| SAHA | 4.13 ± 1.0 | 78.3 ± 6.8 | 11.5 ± 1.2 | 2.0 ± 0.5 |
| Doxo | 19.4 ± 2.4 * | 49.0 ± 4.2 * | 28.2 ± 3.5 | 0.1 ± 0.04 |
| SAHA + Doxo | 4.72 ± 0.5 * | 66.7 ± 5.5 * | 25.1 ± 3.2 | 0.41 ± 0.12 |

5. SAHA Decreased in CTV-1 Cells the Expression of CHK-1 and p-CHK-1, which Might be Induced to Increase by Doxo.

Western blots of CtIP, p-CtIP, CHK-1, p-CHK-1, Chk-2, pChk-2 in CTV-1 cell treated with SAHA, Doxo, or combination of both, at IC50 for 0, 8, 12, 16 hours were observed. It was found that the expression of CHK-1 and p-CHK-1 in CTV-1 cells was increased with time after exposure to Doxo, while was decreased with SAHA treatment beyond 12 hours, comparing to those treated with Doxo only or before treatment (no figure shown).

6. Differential Expression of CHK-1 in J5, PLC and Hep3B HCC Cells Intrinsic CHK-1 Expression was Relatively Low in Hep3B Independently with Time.

Figure 5A:
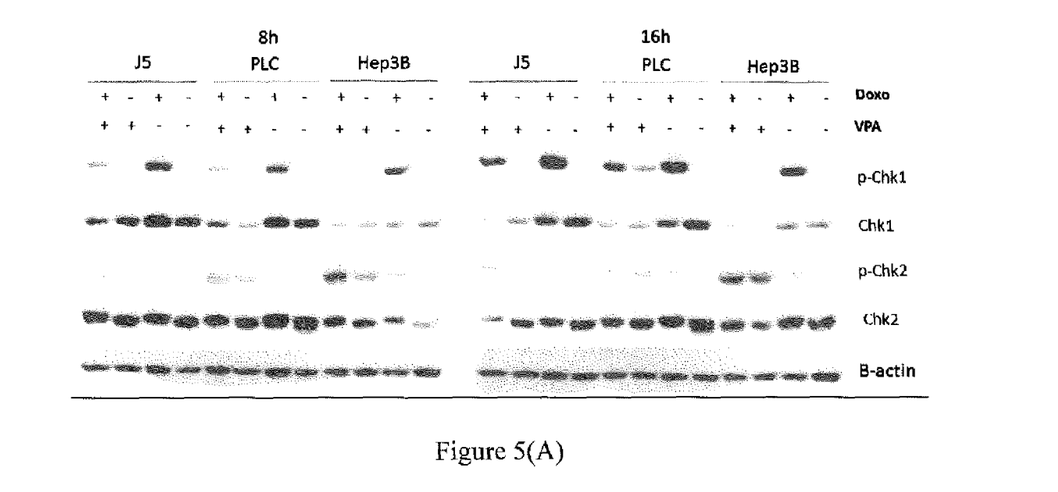
FIG. 5(A) provides the representative western blots for CHK-1, p-CHK-1, CHK-2 and p-CHK-2 in J5, PLC, Hep3B HCC cells treated with vehicles only (Doxo: -, and VPA: -), VPA, Doxo, or both VPA and Doxo, wherein the low intrinsic CHK-1 expression (Doxo: -, and VPA: -) led to relatively low p-CHK-1 expression in Hep3B cells comparing to in J5 and PLC cells.
Figure 5B:
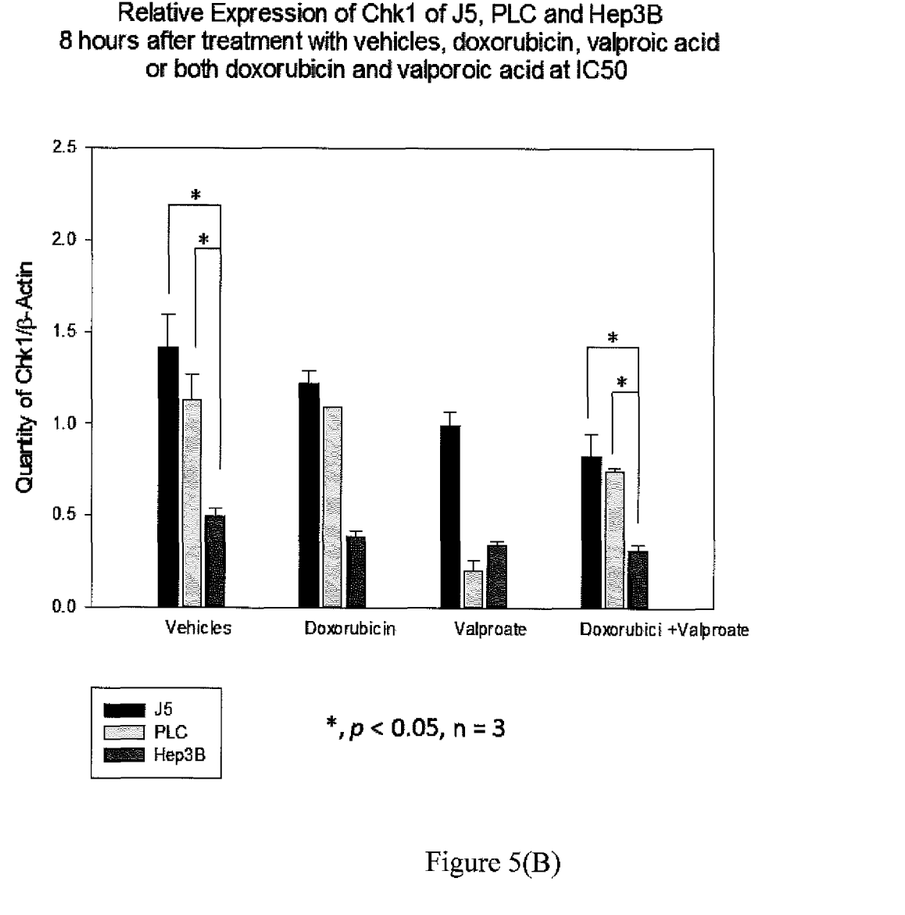
FIG. 5(B) shows the result of the CHK-1 expression standardized by loading quantities, indicating that the expression of CHK-1 was significantly low in Hep3B cells without exposure to VPA or Doxo or exposure to both Doxo and VPA.
Figure 5C:
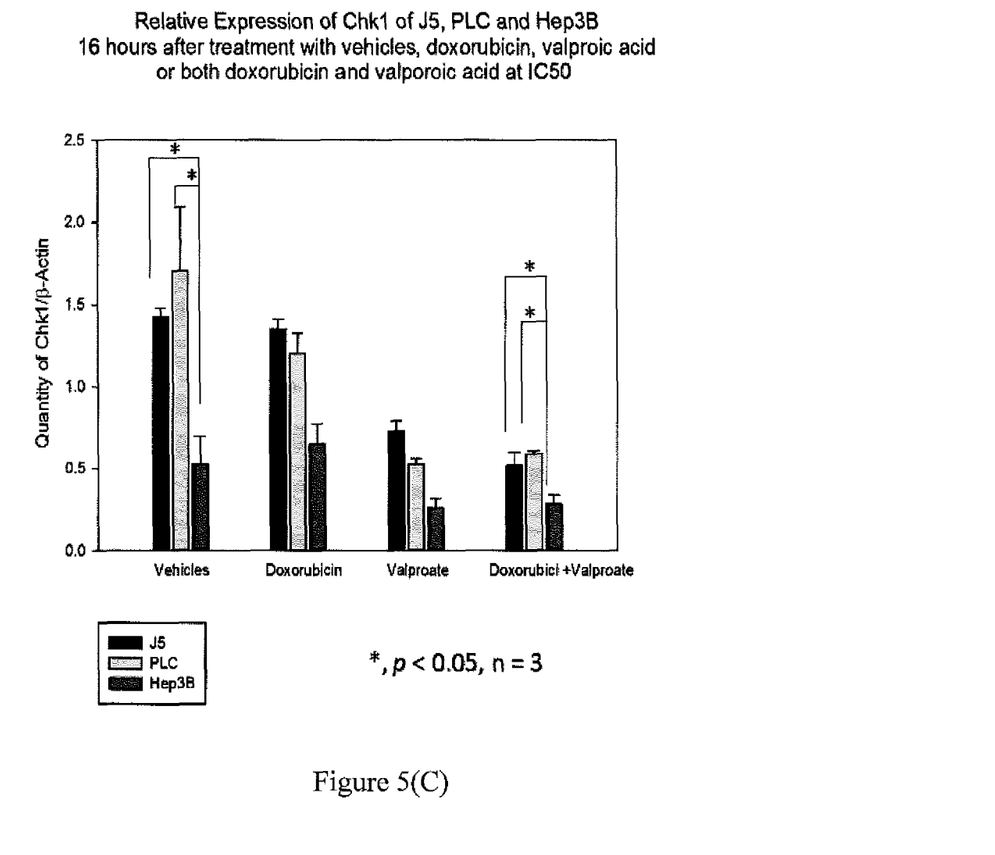

Relatively low expression was noted in Hep3B cells, in which exposure to VPA and Doxo showed synergistic cytotoxicity; while relatively high expression in J5 and PLC cells, in which VPA and Doxo showed only additive and sub-additive cytotoxicities respectively. As shown in FIGS. 5(A) and (B), (A), two representative western blots for CHK-1, p-CHK-1, CHK-2 and p-CHK-2 in J5, PLC, Hep3B HCC cells treated with vehicles only (Doxo: -, and VPA: -), VPA, Doxo, or both VPA and Doxo. Low intrinsic CHK-1 expression (Doxo: -, and VPA: -) showed the p-CHK-1 expression was the relatively low in Hep3B cells as compared to in J5 and PLC cells. (B) and (C). It was indicated that CHK-1 expression was significantly low in Hep3B cells without exposure to VPA or Doxo or exposure to both Doxo and VPA.

Given the above, it is concluded that the synergistic cytotoxic effects of Doxo in combination with SAHA were found in CTV-1 and Molt-3 T-ALL cells, in which the expression and phosphorylation of CHK-1 were negatively affected by SAHA. In the SAHA-treated T-ALL cells, the repair of Doxo-induced DSB was associated with increased γH2AX. However, although SAHA increased expression of γH2AX, apoptosis was enhanced with shortened G0G1 arrest, and low expression of CtIP and also the hampered nuclear entry of CtIP. The hampered entry of CtIP into nuclei was revealed by immunofluorescent confocal microscopy. HDACi thus synergistically impaired the topoisomerase inhibitor II-induced DSB repair and enhanced apoptosis by aborting the DNA repair and inducing apoptosis by hampering the nuclear entry of CtIP. Low intrinsic CHK-1 expression, which was usually accompanied by attenuated CHK-1 phosphorylation, may be potentially a biomarker of synergistic cytotoxicities of HDACi in combination with DSB-inducing chemotherapeutics. Extending the implication of low CHK-1 expression to synergistic effects of the other HDACi, valproic acid (VPA), in combination with Doxo in advanced HCC treatment, as reported in 2015 ASCO meeting abstract, we employed J5, PLC and Hep3B, HCC cell lines to check if low intrinsic CHK-1 expression still correlated with synergistic effects of VPA and Doxo on HCC cells. We found only in Hep3B but not in J5 and PLC cells, VPA in combination with Doxo showed synergistic effects evidenced by isobologram analysis for drug interaction. Further analyses, we found relatively low intrinsic CHK-1 expression significantly occurred in Hep3B cells in comparison to that in J5 and PLC cells, in which we showed no synergistic effects of VPA in combination with Doxo. Low CHK-1 expression thus could be regarded as a biomarkers to predict synergistic effects of HDACis, such as VPA and SAHA, in combination with chemotherapeutic agents which induce double strained DNA break.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:

1. A method for treating a cancer and prolonging the overall survival of a subject suffering a cancer comprising:
   providing a cancer cell sample of the subject, and determining the expression of checkpoint kinase 1 (CHK-1) of the sample, wherein the attenuation of activated CHK-1 is used as a biomarker; and
   administering to the subject, if the attenuation of activated CHK-1 is found in the sample, a combination of doxorubicin (Doxo) and valproic acid (VPA) at the ratio to provide synergistic cancer cell-killing effects and prolonged overall survival.

2. A method according to claim 1, wherein the subject suffering a cancer is administered with the combination of Doxo and VPA after the treatment of a chemotherapy.

3. The method of claim 1, wherein the cancer is hepatocellular carcinoma (HCC).

* * * * *